(12) United States Patent
Miesel et al.

(10) Patent No.: US 8,317,770 B2
(45) Date of Patent: Nov. 27, 2012

(54) SYSTEMS AND METHODS OF IDENTIFYING CATHETER MALFUNCTIONS USING PRESSURE SENSING

(75) Inventors: Keith A. Miesel, St. Paul, MN (US); Eric J. Panken, Edina, MN (US)

(73) Assignee: Medtronic, Inc., Minneapolis, MN (US)

( * ) Notice: Subject to any disclaimer, the term of this patent is extended or adjusted under 35 U.S.C. 154(b) by 1642 days.

(21) Appl. No.: 11/731,355

(22) Filed: Mar. 30, 2007

(65) Prior Publication Data
US 2007/0270782 A1 Nov. 22, 2007

Related U.S. Application Data

(60) Provisional application No. 60/789,729, filed on Apr. 6, 2006.

(51) Int. Cl.
*A61M 31/00* (2006.01)
*A61M 37/00* (2006.01)

(52) U.S. Cl. .......... 604/500; 604/65; 604/67; 604/151

(58) Field of Classification Search ............... 604/151, 604/65, 67, 500, 501
See application file for complete search history.

(56) References Cited

U.S. PATENT DOCUMENTS

| | | | |
|---|---|---|---|
| 3,882,443 A | 5/1975 | Mortia | |
| 4,137,913 A * | 2/1979 | Georgi | 604/67 |
| 4,373,527 A | 2/1983 | Fischell | |
| 4,388,833 A | 6/1983 | Kuwayama | |
| 4,530,696 A | 7/1985 | Bisera et al. | |
| 4,534,756 A | 8/1985 | Nelson | |
| 4,551,133 A | 11/1985 | Zegers de Beyl | |
| 4,619,653 A | 10/1986 | Fischell | |
| 4,710,163 A * | 12/1987 | Butterfield | 604/65 |
| 4,714,462 A | 12/1987 | DiDomenico | |
| 4,784,645 A | 11/1988 | Fischell | |
| 4,979,940 A | 12/1990 | Bobo, Jr. | |
| 5,006,997 A | 4/1991 | Reich | |
| 5,024,668 A | 6/1991 | Peters et al. | |
| 5,040,536 A | 8/1991 | Riff | |

(Continued)

FOREIGN PATENT DOCUMENTS

EP 0 248 632 12/1987

(Continued)

OTHER PUBLICATIONS

"The SynchroMed Pump" datasheet, [online]. Medtronic, Inc., Minneapolis, MN, Version b3.01, [retrieved on Oct. 19, 2007]. Retrieved from the Internet:<URL: http://www.medtronic.com/neuro/paintherapies/pain_treatment_ladder/drug_infusion/pumps_pump_sel/synchromed_pumps.html>; 4 pgs.

(Continued)

*Primary Examiner* — Nicholas Lucchesi
*Assistant Examiner* — Ian Holloway
(74) *Attorney, Agent, or Firm* — Mueting Raasch & Gebhardt PA

(57) ABSTRACT

Methods and systems for determining whether a catheter malfunction is present in a catheter by analyzing changes in the pressure of fluids being pumped through the delivery lumen of the catheter. The pressure changes that may be monitored may include, e.g., the peak pressure within the catheter and/or the pressure decay profile. The catheter malfunctions that may be determined using the methods and systems of the invention may include, e.g., leaks, blockages, the presence of gas bubbles, etc.

28 Claims, 7 Drawing Sheets

U.S. PATENT DOCUMENTS

| | | |
|---|---|---|
| 5,059,171 A | 10/1991 | Bridge |
| 5,078,682 A | 1/1992 | Miki |
| 5,087,245 A | 2/1992 | Doan |
| 5,096,385 A | 3/1992 | Georgi |
| 5,116,203 A | 5/1992 | Natwick |
| 5,158,547 A | 10/1992 | Doan |
| 5,176,631 A | 1/1993 | Koenig |
| 5,190,522 A | 3/1993 | Wojcicki et al. |
| 5,205,819 A | 4/1993 | Ross |
| 5,207,666 A | 5/1993 | Idriss |
| 5,276,610 A | 1/1994 | Maeda |
| 5,279,544 A | 1/1994 | Gross et al. |
| 5,290,231 A | 3/1994 | Marcadis |
| 5,328,460 A | 7/1994 | Lord |
| 5,336,181 A | 8/1994 | Nakao |
| 5,342,298 A | 8/1994 | Michaels et al. |
| 5,356,378 A | 10/1994 | Doan |
| 5,496,273 A | 3/1996 | Pastrone |
| 5,501,665 A | 3/1996 | Jhuboo |
| 5,535,752 A | 7/1996 | Halperin et al. |
| 5,605,545 A | 2/1997 | Nowosielski et al. |
| 5,609,576 A | 3/1997 | Voss |
| 5,645,734 A * | 7/1997 | Kenley et al. ............... 210/805 |
| 5,669,877 A | 9/1997 | Blomquist |
| 5,695,473 A | 12/1997 | Olsen |
| 5,800,387 A | 9/1998 | Duffy |
| 5,827,223 A | 10/1998 | Butterfield |
| 5,853,386 A | 12/1998 | Davis |
| 5,893,838 A | 4/1999 | Daoud et al. |
| 5,899,873 A | 5/1999 | Jones et al. |
| 5,906,589 A | 5/1999 | Gordon |
| 5,928,195 A | 7/1999 | Malamud et al. |
| 5,935,106 A | 8/1999 | Olsen |
| 6,152,898 A | 11/2000 | Olsen |
| 6,203,523 B1 | 3/2001 | Haller et al. |
| 6,213,972 B1 | 4/2001 | Butterfield |
| 6,241,704 B1 | 6/2001 | Peterson et al. |
| 6,358,225 B1 | 3/2002 | Butterfield |
| 6,394,986 B1 | 5/2002 | Millar |
| 6,423,029 B1 | 7/2002 | Elsberry |
| 6,423,035 B1 | 7/2002 | Das |
| 6,458,102 B1 | 10/2002 | Mann |
| 6,464,687 B1 | 10/2002 | Ishikawa |
| 6,485,465 B2 | 11/2002 | Moberg |
| 6,551,290 B1 | 4/2003 | Elsberry et al. |
| 6,609,071 B2 | 8/2003 | Shapiro |
| 6,620,151 B2 | 9/2003 | Blischak |
| 6,648,821 B2 | 11/2003 | Lebel |
| 6,716,193 B1 | 4/2004 | Neftel |
| 6,740,059 B2 | 5/2004 | Flaherty |
| 6,742,999 B1 | 6/2004 | Nusser |
| 6,966,325 B2 | 11/2005 | Erickson |
| 7,022,116 B2 | 4/2006 | Morris |
| 7,054,782 B2 | 5/2006 | Hartlaub |
| 7,092,797 B2 | 8/2006 | Gaines |
| 7,104,763 B2 | 9/2006 | Bouton |
| 7,118,565 B2 | 10/2006 | Abboud |
| 7,255,680 B1 | 8/2007 | Gharib |
| 7,255,685 B2 | 8/2007 | Vanderveen |
| 7,291,126 B2 | 11/2007 | Shekalim |
| 7,311,693 B2 | 12/2007 | Shekalim |
| 7,320,676 B2 | 1/2008 | Miesel |
| 7,437,644 B2 | 10/2008 | Ginggen |
| 7,452,190 B2 | 11/2008 | Bouton |
| 7,505,869 B2 | 3/2009 | Hartlaub |
| 7,621,878 B2 | 11/2009 | Ericson |
| 7,722,574 B2 * | 5/2010 | Toman et al. ............... 604/247 |
| 7,998,111 B2 * | 8/2011 | Moberg et al. ............... 604/67 |
| 2001/0034502 A1 | 10/2001 | Moberg |
| 2002/0040208 A1 | 4/2002 | Flaherty |
| 2002/0072733 A1 | 6/2002 | Flaherty |
| 2002/0077581 A1 | 6/2002 | Davidner et al. |
| 2002/0087115 A1 | 7/2002 | Hartlaub |
| 2002/0107477 A1 | 8/2002 | Kipfer |
| 2002/0120236 A1 | 8/2002 | Diaz |
| 2002/0173773 A1 | 11/2002 | Olsen |
| 2003/0073954 A1 | 4/2003 | Moberg |
| 2003/0078547 A1 | 4/2003 | Shekalim |
| 2003/0088238 A1 | 5/2003 | Poulsen |
| 2003/0125662 A1 | 7/2003 | Bui |
| 2003/0135154 A1 | 7/2003 | Heiniger |
| 2003/0236489 A1 | 12/2003 | Jacobson |
| 2004/0034331 A1 * | 2/2004 | Toman et al. ............... 604/500 |
| 2004/0044305 A1 | 3/2004 | Hughett |
| 2004/0085215 A1 | 5/2004 | Moberg |
| 2004/0087894 A1 | 5/2004 | Flaherty |
| 2004/0127844 A1 | 7/2004 | Flaherty |
| 2004/0220548 A1 | 11/2004 | Heruth et al. |
| 2004/0260233 A1 | 12/2004 | Garibotto |
| 2004/0260234 A1 | 12/2004 | Srinivasan |
| 2005/0075624 A1 | 4/2005 | Miesel |
| 2005/0090799 A1 | 4/2005 | Morris |
| 2005/0123420 A1 | 6/2005 | Richter |
| 2005/0192529 A1 | 9/2005 | Butterfield |
| 2005/0209512 A1 | 9/2005 | Heruth et al. |
| 2005/0209513 A1 | 9/2005 | Heruth et al. |
| 2005/0222643 A1 | 10/2005 | Heruth |
| 2005/0234514 A1 | 10/2005 | Heruth et al. |
| 2005/0234518 A1 | 10/2005 | Heruth et al. |
| 2005/0241387 A1 | 11/2005 | Miesel et al. |
| 2005/0245858 A1 | 11/2005 | Miesel |
| 2005/0267413 A1 | 12/2005 | Wang |
| 2006/0161376 A1 | 7/2006 | Hartlaub |
| 2006/0184154 A1 * | 8/2006 | Moberg et al. ............... 604/506 |
| 2006/0271029 A1 | 11/2006 | Abboud |
| 2006/0282040 A1 * | 12/2006 | Toman et al. ............... 604/151 |
| 2007/0060871 A1 | 3/2007 | Istoc |
| 2007/0078381 A1 | 4/2007 | Yap |
| 2007/0149926 A1 | 6/2007 | Moberg |
| 2007/0191770 A1 | 8/2007 | Moberg |
| 2007/0244469 A1 * | 10/2007 | Ozeri et al. ............... 604/891.1 |
| 2007/0270782 A1 | 11/2007 | Miesel |
| 2007/0274843 A1 | 11/2007 | Vanderveen |
| 2008/0009837 A1 | 1/2008 | Miesel |
| 2008/0097287 A1 | 4/2008 | Nelson |
| 2008/0139996 A1 | 6/2008 | Bowman |
| 2008/0167641 A1 | 7/2008 | Hansen |
| 2008/0221522 A1 * | 9/2008 | Moberg et al. ............... 604/151 |
| 2008/0221523 A1 * | 9/2008 | Moberg et al. ............... 604/151 |
| 2009/0082757 A1 | 3/2009 | Rogers |
| 2010/0037680 A1 * | 2/2010 | Moberg et al. ............... 73/37 |
| 2011/0077605 A1 * | 3/2011 | Karpowicz et al. ............... 604/318 |

FOREIGN PATENT DOCUMENTS

| | | |
|---|---|---|
| EP | 0 248 633 | 12/1987 |
| EP | 0 248 633 A2 | 12/1987 |
| EP | 0248632 A2 | 12/1987 |
| EP | 0 248 633 A3 | 2/1989 |
| EP | 0248632 A3 | 3/1989 |
| EP | 0 328 162 | 8/1989 |
| EP | 0 328 162 A2 | 8/1989 |
| EP | 0 328 162 A3 | 10/1989 |
| EP | 0 328 162 B1 | 2/1993 |
| EP | 0 248 633 B1 | 8/1994 |
| EP | 0 522 527 | 12/1994 |
| EP | 0 856 326 | 8/1998 |
| EP | 0 856 326 A1 | 8/1998 |
| EP | 0 621 791 | 8/2000 |
| EP | 1 342 481 | 9/2003 |
| EP | 1 535 637 | 6/2005 |
| EP | 0 993 268 | 11/2005 |
| EP | 1 839 695 | 10/2007 |
| EP | 1 592 468 | 9/2008 |
| WO | WO 95/32013 | 11/1995 |
| WO | WO 99/55225 | 11/1999 |
| WO | WO 00/44420 | 8/2000 |
| WO | WO 02/064040 | 8/2002 |
| WO | WO 02/064040 A2 | 8/2002 |
| WO | WO 02/070047 | 9/2002 |
| WO | WO 02/064040 A2 | 11/2002 |
| WO | WO 02/064040 A3 | 5/2003 |
| WO | WO 2005/072792 | 8/2005 |
| WO | WO 2005/089860 | 9/2005 |
| WO | WO 2005/089860 A1 | 9/2005 |
| WO | WO 2005/119181 | 12/2005 |
| WO | WO 2006/067217 | 6/2006 |

| | | |
|---|---|---|
| WO | WO 2006/108775 | 10/2006 |
| WO | WO 2007/020029 | 2/2007 |
| WO | WO 2007/020029 A1 | 2/2007 |

OTHER PUBLICATIONS

U.S. Appl. No. 12/623,484, filed Nov. 23, 2009, Our Ref: P0036051.00.

U.S. Appl. No. 11/731,356, filed Mar. 30, 2007, Our Ref: P0023972.00.

U.S. Appl. No. 11/778,400, filed Jul. 16, 2007, Our Ref: P0020204.00.

Giepel et al., "Design of an Implantable Active Microport System for Patient Specific Drug Release", Proceedings of the 24$^{th}$ IASTED International Mutli-Conference on Biomedical Engineering (The International Association of Science and Technology for Development), Feb. 15-17, 2006, Innsbruck, Austria; pp. 161-166.

"The SynchroMed Pump" datasheet, [online], Medtronic, Inc., Minneapolis, MN, Version b3.01, [retrieved on Oct. 19, 2007]. Retrieved from the Internet:URL:http://www.medtronic.com/neuro/paintherapies/pain_treatment_ladder/drug_infusion/pumps_pum_sel/synchromed_pumps:html; 4 pgs.

Geipel et al., "Design of an implantable active microport system for patient specific drug release", Proceedings of the 24$^{th}$ IASTED International Multi-conference on Biomedical Engineering (The International Association of Science and Technology for Development), Feb. 15-17, 2006, Innsbruck, Austria; pp. 161-166.

U.S. Appl. No. 11/731,356, filed Mar. 30, 2007, Miesel et al.

* cited by examiner

SYSTEMS AND METHODS OF IDENTIFYING CATHETER MALFUNCTIONS USING PRESSURE SENSING

RELATED APPLICATION

The present application claims the benefit under 35 U.S.C. Section 119(e) of U.S. Provisional Patent Application Ser. No. 60/789,729, filed Apr. 6, 2006 and titled SYSTEMS AND METHODS OF IDENTIFYING CATHETER MALFUNCTIONS USING PRESSURE SENSING, which is hereby incorporated by reference in its entirety.

TECHNICAL FIELD

The present invention relates generally to pressure sensing in implantable medical devices and, more particularly, to pressure sensing in implantable medical devices delivering a fluid to a patient and using the sensed pressure to determine the occurrence of malfunctions in the catheter.

BACKGROUND

Implantable drug delivery or infusion devices and/or systems are commonly used, for example when chronic administration of a pharmaceutically active agent or therapeutic substance to a patient is required. An implantable infusion pump-catheter delivery system may be preferred when it is important to deliver the agent to a specific site or when the agent must be administered to spaced sites in tightly controlled, yet minute dosages.

Typically, an implantable therapeutic substance delivery device has a reservoir for holding a supply of therapeutic substance awaiting delivery to a delivery site in the patient. A pump may be fluidly coupled to the reservoir for creating fluidic pressure to facilitate delivery of the therapeutic substance to the patient. A catheter provides a pathway for delivering the therapeutic substance to the delivery site in the patient.

All parts of the therapeutic substance delivery device/system need to operate adequately to ensure proper functioning of the device/system. While perhaps the least complex, catheters can have and can develop operational problems.

Sometimes catheters in such delivery systems can become obstructed or clogged. A partial or complete blockage could prevent the therapeutic substance from reaching the delivery site in the patient or, in the case of a partial obstruction, could prevent an adequate supply of the therapeutic substance from reaching the delivery site in the patient.

Catheters can also leak due to cuts, tears, etc. A leak, small or large, can also prevent the therapeutic substance from reaching the delivery site in the patient. A leak can result in a double problem. In addition to the lack of therapeutic substance supplied to the delivery site of the patient, the therapeutic substance could be dispersed elsewhere in the body of the patient which may create further issues.

It has, however, been difficult to detect the malfunction of a catheter. For example, if the catheter has a leakage, the implantable delivery device could continue to deliver therapeutic substance and there may be no way to know that the therapeutic substance was not reaching the desired delivery site. The patient may not receive the benefit of the therapeutic substance but might not know why. As another example, if the catheter has an obstruction, the implantable delivery device might cease to deliver the therapeutic substance. But it may be difficult to know why the failure occurred. The failure to deliver might have been caused by other factors, such as power failure, pump failure, an empty reservoir, etc.

SUMMARY OF THE INVENTION

The present invention provides a variety of methods and systems for determining whether a catheter malfunction is present in a catheter by analyzing changes in the pressure of fluids being pumped through the delivery lumen of the catheter. The pressure changes that may be monitored may include, e.g., the peak pressure within the catheter and/or the pressure decay profile. The catheter malfunctions that may be determined using the methods and systems of the invention may include, e.g., leaks, blockages, the presence of gas bubbles, etc.

The methods of the present invention are adapted for use in systems in which a fluid is delivered through an implanted catheter using pulses. As used herein, the term "pulse" may include any change in the rate of fluid delivery that is capable of providing a pressure curve that can be used to determine a catheter malfunction. For example, a pulse may be an event in which a discrete bolus of fluid is delivered into the lumen of the catheter, where each pulse is separated from the preceding and succeeding pulses by a period of time during which no fluid is delivered into the lumen. Pulses may also be delivered by pumping mechanisms that do not deliver discrete boluses (such as, e.g., peristaltic pumps, etc.). In such cases, a "pulse" may be a change in the rate of fluid delivery, but in which successive pulses are not necessarily separated by periods in which no fluid is delivered. For example, if a pump mechanism rate is increased (e.g., by a factor of two or more) and that rate increase causes a corresponding pressure increase in the fluid delivered into the lumen of the catheter, then any such rate change and the pump mechanism used to create it can be used in connection with present invention. In such an embodiment, the pump mechanism rate may alternately be increased and decreased in multiple cycles if multiple pulses are needed.

Each pulse of fluid delivered into the catheter by the pump mechanism will generate a pressure curve indicative of a variety of conditions in the catheter. The pressure curve in a catheter is a function of a variety of factors including, e.g., the length of the fluid path between the pump mechanism and the delivery section of the catheter, the compliance or elasticity of the catheter lumen, flow restrictors in the fluid path (if any), etc. When the catheter is disconnected from the pump mechanism, develops a leak, becomes blocked, or includes a gas bubble, a characteristic pressure curve can be detected. The characteristics relied on may include the peak pressure detected after delivery of a pulse, the decay time required for the detected pressure to fall from the peak pressure to a threshold pressure, or a combination of both peak pressure and decay time.

As discussed in more detail herein, the methods may be performed in real-time or the pressure data may be stored to allow for analysis at a later time. If performed in real-time, the infusion device may preferably include hardware and/or software to allow for the required functions.

In one aspect, the present invention provides a method of identifying the presence of a catheter malfunction. The method includes delivering pulses of a fluid into a delivery lumen of an implanted catheter; measuring decay time after a selected pulse, wherein the decay time is the time required for pressure within the delivery lumen to fall below a selected threshold pressure value after a selected event corresponding to the selected pulse; comparing the decay time to a selected decay time; and determining the existence of a catheter malfunction in the form of a leak in the catheter if the decay time is below the selected decay time.

In another aspect, the present invention provides a method of identifying the presence of a catheter malfunction. The method includes delivering pulses of a fluid into a delivery lumen of an implanted catheter; and measuring decay time after a selected pulse, wherein the decay time is the time required for pressure within the delivery lumen to fall below a selected threshold pressure value after a selected event corresponding to the selected pulse, wherein the measuring includes assigning a timeout value to the decay time if the pressure within the delivery lumen does not fall below the selected threshold pressure value after a selected timeout time.

In another aspect, the present invention provides a method of identifying the presence of a catheter malfunction. The method includes delivering pulses of a fluid into a delivery lumen of an implanted catheter; measuring decay time after a selected pulse, wherein the decay time is the time required for pressure within the delivery lumen to fall below a selected threshold pressure value after a selected event corresponding to the selected pulse; assigning a timeout value to the decay time if the pressure within the delivery lumen does not fall below the selected threshold pressure value after a selected timeout time; comparing the decay time to a selected decay time; determining the existence of a catheter malfunction in the form of a leak in the catheter if the decay time is below the selected decay time; and determining the existence of a catheter malfunction in the form of a blockage in the delivery lumen if the decay time is assigned the timeout value.

In another aspect, the present invention provides a method of identifying the presence of a catheter malfunction. The method includes delivering pulses of a fluid into a delivery lumen of an implanted catheter; measuring peak pressure within the delivery lumen after a selected pulse; comparing the measured peak pressure to a selected peak pressure value; and determining the existence of a catheter malfunction in the form of a disconnected catheter if the measured peak pressure value is below the selected peak pressure value.

In another aspect, the present invention provides a method of determining the presence of a catheter malfunction. The method includes delivering pulses of a fluid into a delivery lumen of an implanted catheter; measuring peak pressure within the delivery lumen after a selected pulse; comparing the measured peak pressure to a selected peak pressure value; determining the existence of a catheter malfunction in the form of a disconnected catheter if the measured peak pressure value is below the selected peak pressure value after comparing the measured peak pressure to the selected peak pressure; measuring decay time after a selected pulse, wherein the decay time is the time required for pressure within the delivery lumen to fall below a selected threshold pressure value after a selected event corresponding to the selected pulse; assigning a timeout value to the decay time if the pressure within the delivery lumen does not fall below the selected threshold pressure value after a selected timeout time; comparing the decay time to a selected decay time after measuring the decay time; determining the existence of a catheter malfunction in the form of a leak in the catheter if the decay time is below the selected decay time; and determining the existence of a catheter malfunction in the form of a blockage in the delivery lumen if the decay time is at the timeout value.

In another aspect, the present invention provides an implantable infusion system including a pump mechanism fluidly coupled to a reservoir to receive fluid contained within the reservoir; a catheter having a delivery lumen fluidly coupled to the pump mechanism, wherein the delivery lumen extends to a delivery region in the catheter; a pressure sensor positioned to monitor fluid pressure within the delivery lumen of the catheter and provide a pressure signal representative of the fluid pressure; and control electronics connected to receive the pressure signal from the pressure sensor. The control electronics measures decay time in the fluid pressure after a selected pulse based on the pressure signal, wherein the decay time is the time required for fluid pressure within the delivery lumen to fall below a selected threshold pressure value after a selected event corresponding to the selected pulse; compares the decay time to a selected decay time; and determines the existence of a catheter malfunction in the form of a leak in the catheter if the decay time is below the selected decay time.

In another aspect, the present invention provides an implantable infusion system that includes a pump mechanism fluidly coupled to a reservoir to receive fluid contained within the reservoir; a catheter having a delivery lumen fluidly coupled to the pump mechanism, wherein the delivery lumen extends to a delivery region in the catheter; a pressure sensor positioned to monitor fluid pressure within the delivery lumen of the catheter and provide a pressure signal representative of the fluid pressure; and control electronics connected to receive the pressure signal from the pressure sensor. The control electronics measures decay time after a selected pulse based on the pressure signal, wherein the decay time is the time required for pressure within the delivery lumen to fall below a selected threshold pressure value after a selected event corresponding to the selected pulse; and assigns a timeout value to the decay time if the fluid pressure within the delivery lumen does not fall below the selected threshold pressure value after a selected timeout time.

In another aspect, the present invention provides an implantable infusion system that includes a pump mechanism fluidly coupled to a reservoir to receive fluid contained within the reservoir; a catheter having a delivery lumen fluidly coupled to the pump mechanism, wherein the delivery lumen extends to a delivery region in the catheter; a pressure sensor positioned to monitor fluid pressure within the delivery lumen of the catheter and provide a pressure signal representative of the fluid pressure; and control electronics connected to receive the pressure signal from the pressure sensor. The control electronics determines peak pressure within the delivery lumen after a selected pulse based on the pressure signal; compares the peak pressure to a selected peak pressure value; and determines the existence of a catheter malfunction in the form of a disconnected catheter if the peak pressure value is below the selected peak pressure value.

The above summary is not intended to describe each embodiment or every implementation of the present invention. Rather, a more complete understanding of the invention will become apparent and appreciated by reference to the following Detailed Description of Exemplary Embodiments and claims in view of the accompanying figures of the drawing.

BRIEF DESCRIPTION OF THE VIEWS OF THE DRAWING

The present invention will be further described with reference to the figures of the drawing.

DETAILED DESCRIPTION OF EXEMPLARY EMBODIMENTS

Figure 1A:
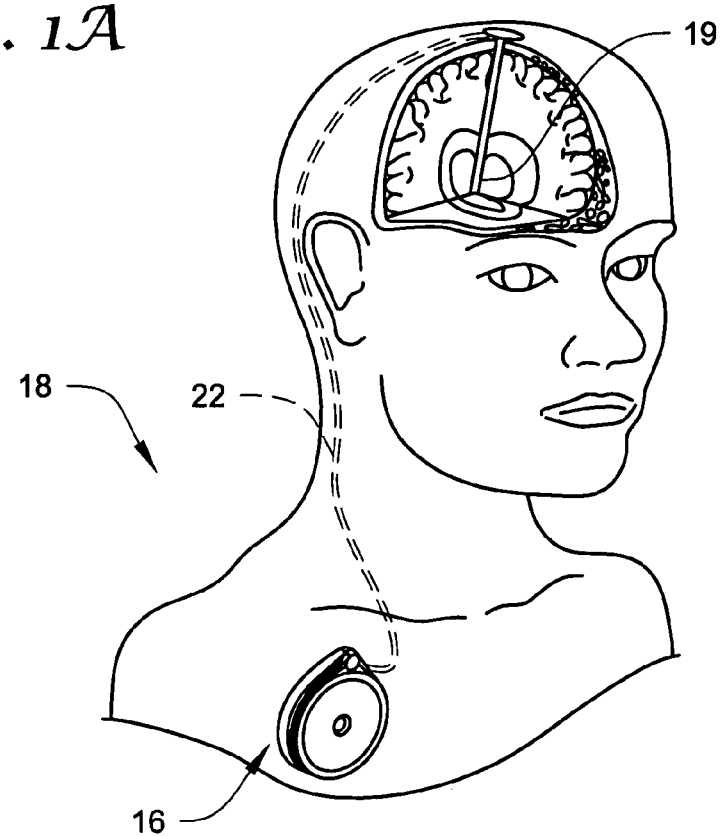
FIG. 1A depicts one exemplary embodiment of an implantable medical device that can be used in connection with the present invention in which the catheter is implanted in the brain of the subject.

In the following detailed description of illustrative embodiments of the invention, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the present invention.

It is noted that the terms "comprises" and variations thereof do not have a limiting meaning where these terms appear in the accompanying description and claims. Moreover, "a," "an," "the," "at least one," and "one or more" are used interchangeably herein.

Relative terms such as left, right, forward, rearward, top, bottom, side, upper, lower, horizontal, vertical, and the like may be used herein and, if so, are from the perspective observed in the particular figure. These terms are used only to simplify the description, however, and not to limit the scope of the invention in any way.

Figure 1B:
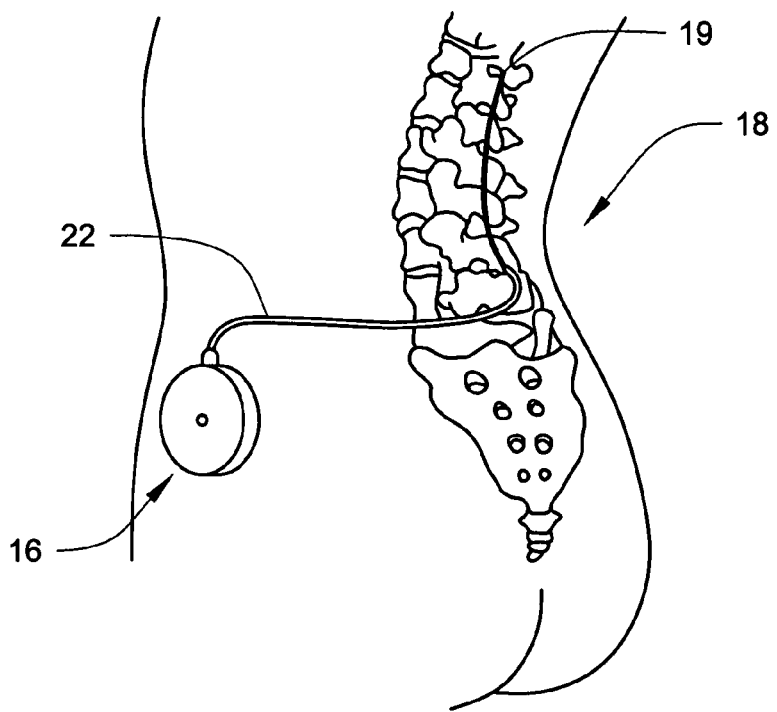
FIG. 1B depicts the implantable medical device of FIG. 1A in which the catheter is implanted in the intrathecal space of the spinal canal of the subject.

FIGS. 1A & 1B illustrate one exemplary embodiment of an implantable infusion system that is implanted within a patient's body 18. The exemplary infusion systems depicted in FIGS. 1A & 1B include a medical device, e.g., implantable medical device 16, and preferably at least one catheter 22. Such infusion systems may be used for a wide variety of therapies including treatment of pain, spasticity, and other medical conditions. Although exemplary infusion systems that may be used in connection with the present invention are described herein, reference may also be had to U.S. Patent Application Publication No. US 2005/0075624 A1, titled PRESSURE SENSING IN IMPLANTABLE MEDICAL DEVICES (Miesel), which describes infusion systems that may be modified for use accordance with the methods of the present invention.

The medical device 16 and catheter 22 are typically implanted by a clinician (e.g., surgeon) within the body 18 during a surgical procedure. While the present invention also contemplates embodiments wherein the catheter is implanted with a proximal end outside the body so that it may attach to an external infusion device, the remainder of this description is, for the sake of brevity, directed to implantable infusion systems that are entirely implanted in the body 18 of the patient.

Before implantation of the medical device 16, the catheter 22 may be positioned such that the fluid delivered to the patient through the catheter 22 reaches a selected internal delivery location 19 within the body 18 of the patient. As depicted in FIG. 1A, the infusion system is implanted such that the delivery site 19 is located within the brain. As depicted in FIG. 1B, the infusion system is implanted such that the delivery site 19 is located within the intrathecal space of the spinal canal. Although FIGS. 1A & 1B depict two potential alternative delivery locations, the infusion systems of the present invention may be used to deliver fluid to any other selected internal delivery location, e.g., epidural, etc.

Catheter 22 may deliver fluid at a location other than at its distal end. For example, catheter 22 may intentionally have a delivery region that is not proximate the distal end of the catheter 22, e.g., a hole or valve positioned somewhere before reaching the distal end of the catheter 22. Thus, catheter 22 may be placed in patient 18 with a delivery region of catheter 22 placed in or near to, generally proximate to, the selected internal delivery site 19.

A proximal end of the catheter 22 may be tunneled through the tissue to the device implant location and coupled to a catheter port of the medical device 16. If implanted, the medical device 16 is typically positioned subcutaneously, e.g., from 1 centimeter (0.4 inches) to 2.5 centimeters (1 inch) beneath the skin, where there is sufficient tissue for supporting the medical device 16, e.g., with sutures or the like.

The medical device 16 is, in the illustrated embodiment, operable to infuse a fluid from an enclosed reservoir into the body 18 through the catheter 22.

Although the fluid may preferably contain one or more therapeutic substances that are to be delivered to a patient through the catheter, the fluids are not required to contain any therapeutic substances. For example, the fluids may be used within the methods and systems to confirm proper catheter functioning without supplying any specific therapeutic effect.

As used herein, the term "therapeutic substance" refers to a substance intended to have a therapeutic effect on the patient, e.g., pharmaceutical compositions, genetic materials, biologics, and other substances. "Phannaceutical compositions," as used herein, may include chemical formulations intended to have a therapeutic effect such as antispasmodics, pain medications, chemotherapeutic agents, and the like. Pharmaceutical compositions are often configured to function effectively in an implanted environment by possessing various characteristics including: stability at body temperature to retain therapeutic qualities; concentration to reduce the frequency of replenishment; and the like. "Genetic materials," as used herein, may include substances intended to have a direct or indirect genetic therapeutic effect such as genetic vectors, genetic regulator elements, genetic structural elements, DNA, and the like. "Biologics," as used herein, may include substances that are living matter, or derived from living matter, and offer a therapeutic effect to the patient such as stem cells, platelets, hormones, biologically produced chemicals, and the like. "Other substances" may include most any other substance that is intended to have a therapeutic effect, yet does not clearly fit within one of the categories identified above. Examples of other substances may include saline solutions, fluoroscopy agents, and the like.

In some embodiments, the fluid contained within a reservoir of the medical device 16 may be replenished periodically after device implantation. Typically, replenishment is accomplished with a non-coring needle (not shown) connected to a syringe filled with the fluid. The needle may be inserted through the patient's skin and into a self-sealing septum located within the housing of the medical device 16.

Figure 2:
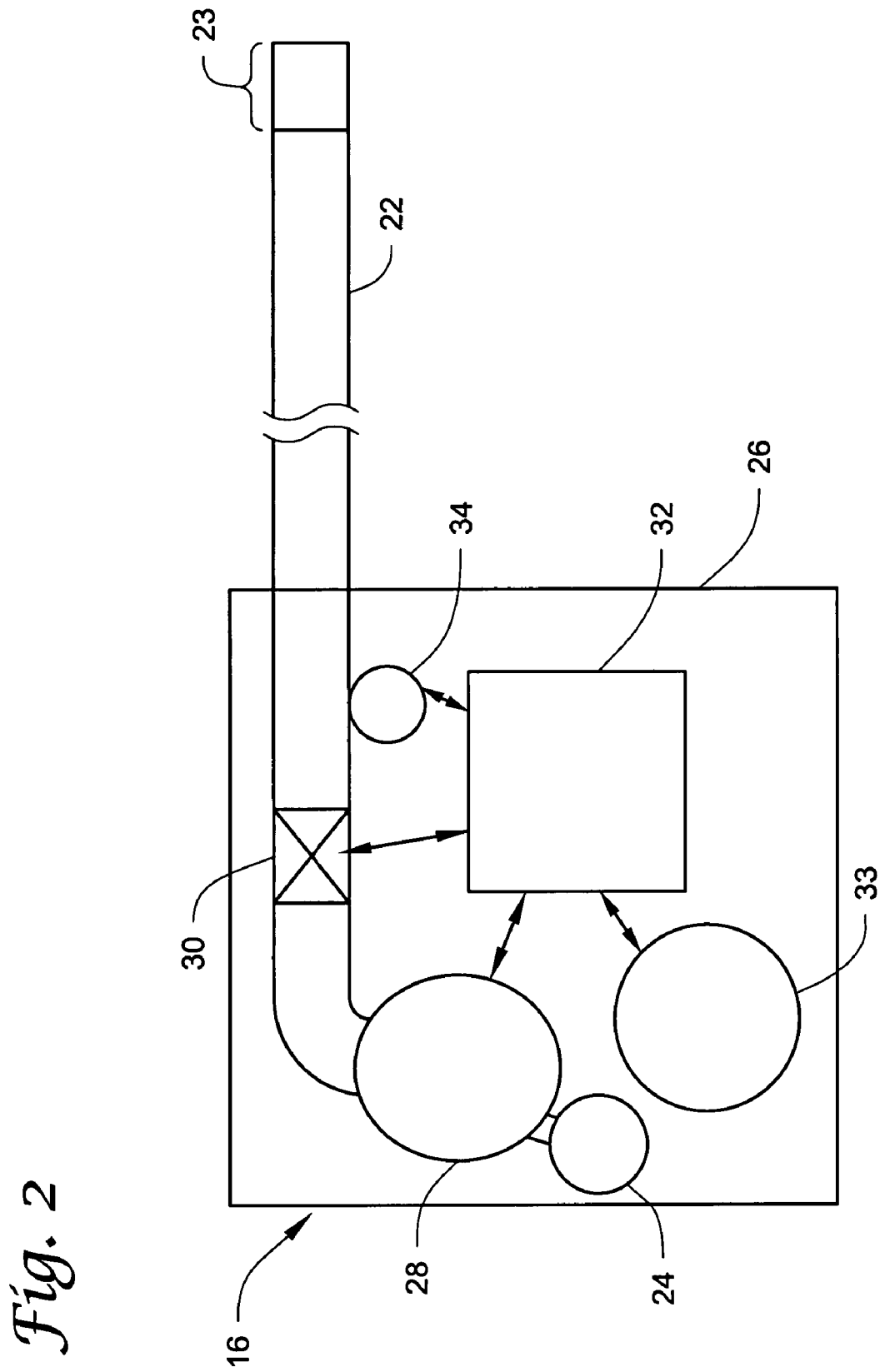
FIG. 2 is a block diagram of an exemplary medical device that can be used in connection with the methods of the present invention.

If catheter 22 malfunctions, i.e., has or develops a leak or an obstruction, that malfunction may be detected by analyzing the pressure of the fluid, typically a liquid, in a lumen of catheter 22. FIG. 2 is a block diagram depicting components that may be included in one exemplary embodiment of the infusion system depicted in FIGS. 1A & 1B.

In the infusion system, fluid is stored in reservoir 24 in housing 26. Pump mechanism 28 is fluidly coupled to reservoir 24 to receive the fluid stored in the reservoir 24. The output of pump mechanism 28 may be coupled to catheter 22 through a check valve 30. Pump mechanism 28 and check valve 30 may be controlled by electronics module 32. Pressure sensor 34 is operatively coupled to detect/sense pressure in a lumen of catheter 22 that is in fluid communication with the delivery region 23 of the catheter. If the pressure sensed by pressure sensor 34 is indicative of a catheter malfunction as discussed herein, then electronics module 32 may take appropriate action such as by sounding alarm 33. A refill port (not shown) may be used to refill reservoir 24 without explanting implantable medical device 16. Various systems for refilling reservoirs are known and are not further discussed herein (see, for example, U.S. Pat. No. 5,158,547 to Doan et al. and U.S. Pat. No. 6,152,898 to Olsen).

The housing 26 of the medical device 16 may be in the form of a single housing manufactured from a biocompatible material such as titanium, tantalum, stainless steel, plastic, ceramic, and/or the like. However, one or more components of the medical device 16 may also be located in separate housings that are appropriately coupled to each other. For example, the reservoir 24 could be attached to or placed within the housing 26, or it could be separated from the housing 26 and provided within a different housing that is connected to housing 26 via, e.g., a fluid coupling.

Although not depicted, the medical device may also include a power source in the form of, e.g., a battery, capacitor, etc. The power source may preferably be operatively connected to supply power to the pump mechanism 28, control electronics 32, alarm 33, pressure sensor 34, and any other devices requiring electric power.

The control electronics 32 may be provided in any suitable form and may, for example, preferably include memory and a controller. The controller may, for example, be an Application Specific Integrated Circuit (ASIC) state machine, a gate array, and/or may include a microprocessor. The control electronics 32 are preferably configured to operate the pump mechanism 28 (e.g., controlling infusion rate, etc.). The control electronics 32 may also include components, etc. to operate other features not depicted in the exemplary system such as valves, sensors (temperature, density, etc.), patient alarms, etc.

The memory provided within the control electronics 32 may be used to store the pressure signal data received from the pressure sensor 34 as a part of the pressure monitoring. The pressure signal data may be stored and analyzed on-board within the control electronics or using a remote device. The memory may be in any suitable format, e.g., flash memory devices, magnetic memory devices, optical data storage devices, etc.

The control electronics 32 may further include telemetry components configured to receive and/or send information after the medical device 16 is implanted in a patient. Telemetry may also be used to transmit any data stored within the control electronics 32 of the infusion system relating to the catheter pressures as discussed herein. The pressure data may be transmitted to allow for analysis of the data, remote data storage (where, e.g., the amount of data may otherwise exceed the data storage capacity within the infusion system itself), etc.

Telemetry may also be used to, e.g., allow programming of the infusion rate, infusion times, etc. Telemetry may further be used to provide information from the infusion device such as, e.g., the amount of fluid in the reservoir, etc. Such information may be used to determine whether the reservoir requires refilling, etc.

The reservoir 24 may take any suitable form such as, e.g., a variable volume reservoir formed by an expandable member. An outer surface of the expandable member of the reservoir 24 may be exposed to ambient body pressure such that the pressure of the fluid within the reservoir 24 can change in response to changes in ambient pressure surrounding the medical device 16. Other embodiments are also possible in which the reservoir 24 is partially or fully contained within the housing 26 such that the pressure of the fluid within the reservoir 24 is isolated from ambient pressure.

The pump mechanism 28 is preferably operably connected to both the reservoir 24 and the proximal end of catheter 22. As a result, the pump mechanism 28 may be operated to transfer fluid from the reservoir 24 to the internal delivery location through the catheter 22. As discussed herein, the pump mechanism 28 is preferably capable of delivering the fluid in the downstream direction towards the delivery region 23 of catheter 22 in discrete pulsed bolus amounts.

Many different pump mechanisms 28 may be used in the medical devices of the present invention. The pump mechanisms may include both passive and active mechanisms. Passive devices may include those that rely on fluid pressure within the reservoir 24 to force the fluid through the catheter (with pulsing provided by, e.g., opening and closing a valve, etc.). Active mechanisms may generally be considered to include devices more commonly considered to be pumps, including but not limited to, e.g., piston pumps, diaphragm pumps, peristaltic pumps, piezoelectric pumps, etc. Examples of some potentially suitable solenoid piston pumps that may be used in connection with the infusion devices of the invention may be described in U.S. Patent Application Publication No. US 2002/0173773 A1, titled PERMANENT MAGNET SOLENOID PUMP FOR AN IMPLANTABLE THERAPEUTIC SUBSTANCE DELIVERY DEVICE (Olsen).

To detect pressure within the delivery lumen of catheter 22, pressure sensor 34 may be placed in fluid contact with a lumen of catheter 22. Pressure sensor 34 may be placed in fluid contact with a lumen of a catheter 22 anywhere along the lumen of the catheter 22. The pressure sensor 34 may be contained within housing 26. Pressure sensor 34 could also be located external to housing 26. Pressure sensor 34 may be coupled to the electronics module 32 as discussed herein. For ease of coupling pressure sensor 34 to the control electronics 32, it may be preferred to locate pressure sensor 34 within housing 26.

The pressure sensor 34 may be adapted to read either gage or absolute pressure of the fluid in the catheter 22. Because the methods of the present invention rely on comparison of pressure developed between successive pulses delivered through the catheter 22, changes in ambient pressure may be of reduced importance in implementing the present invention (especially where the successive pulses are delivered within relatively short time frames, e.g., within minutes or even seconds of each other).

In those instances where, however, it is desirable to use pressure measurements from sensor 34 that are adjusted to account for ambient pressure outside of the catheter 22, a reference pressure may be detected within a patient's 18 body in which catheter 22 is implanted or may be detected outside of patient's 18 body. When detected within a patient's body, a reference pressure may be detected in a location near medical device 16 or delivery location 19, or even in a location in a separate area of the patient's 18 body. A reference pressure may be obtained in any location capable of providing a pressure indicative of the external environment of implanted catheter 22. In some embodiments, an infusion system may include a catheter 22 having a first lumen for delivering a fluid and a second lumen through which no fluid is delivered. A reference pressure may then be detected in the second lumen. The second lumen in catheter 22 can easily be used to obtain a reference pressure from a distal end of catheter 22, from a delivery region of catheter 22 and/or from delivery location 19. Further discussions regarding reference pressures may be found in U.S. Patent Application Publication No. US 2005/0075624 A1, titled PRESSURE SENSING IN IMPLANTABLE MEDICAL DEVICES (Miesel).

Any pressure sensor 34 capable of measuring the fluid pressure within a delivery lumen of the catheter 22 and providing a pressure signal representative of the fluid pressure (to, e.g., the control electronics 32) may be used in connection with the present invention. Although only one pressure sensor 34 is depicted in FIG. 2, the systems and/or methods of the present invention may use two or more pressure sensors. Some potentially suitable pressure sensor constructions may be described in, e.g., U.S. Patent Application Publication No. US 2005/0075624 A1, titled PRESSURE SENSING IN IMPLANTABLE MEDICAL DEVICES (Miesel).

Even though the use of pressure measurements during pulsed delivery may be capable of correcting for some changes in ambient pressure by measuring relative to a baseline pressure as discussed herein, in some instances rapid fluctuations in baseline pressure within the catheter could potentially result in pressure readings that are not indicative of the pressure developed within the catheter as a result of the fluid pumped through the catheter. If, for example, the delivery region of the catheter is located with the Cerebrospinal Fluid (CSF) of a patient, large, rapid fluctuations in CSF pressure could confound the measurement of both pressure amplitude and decay times because those fluctuations could change the baseline pressure to such a degree that the pressure amplitude and/or decay times are no longer indicative of the catheter function alone.

Because instability or changes in baseline pressure within the catheter may result in erroneous results when attempting to identify catheter malfunctions, the baseline pressure within the catheter may be monitored shortly before a pulse delivery event is to occur. If measured shortly before a pulse delivery event, the methods of the invention may involve a resetting or determination of baseline pressure before a selected pulse delivery event (and typically after a pulse delivery event that precedes the selected pulse delivery event). Resetting or new determination of a baseline pressure shortly before a selected pulse delivery event may assist in compensating for, e.g., low frequency drift in the pressure sensor, posture changes, elevation changes, etc.

If the baseline pressure appears to be unstable, the pulse delivery event can be delayed until the baseline pressure is more stable. In some instances, though, the infusion system could continue to provide a pulse delivery event even though the baseline pressure may be subject to fluctuations. Any pressure data observed and/or stored during such times could, however, be disregarded or at least flagged as potentially erroneous. For example, data could be plotted as a different color, or plotted as a dashed line instead of solid, etc, to indicate that the data is suspect.

If it is determined that the baseline pressure fluctuations could be caused by, e.g., activity and/or posture changes of the patient, the accumulation of pressure data could be delayed until posture is stable and/or activity level is low. In some instances, input from another sensor, one or more accelerometers, could be used to determine posture and/or activity levels.

Although not depicted, the catheter 22 may include a separate flow restrictor to increase back pressure within the catheter 22. A separate flow restrictor, however, may not be necessary in some embodiments of the present invention where, for example the delivery lumen in the catheter and/or the delivery region of the catheter provide sufficient back pressure in the absence of a separate flow restrictor. The pulsed nature of the fluid delivery through the catheter may enhance the pressure pulse produced from the inherent flow restrictions present in the infusion system, thus allowing the use of a catheter that is free of flow restrictor elements (i.e., elements whose primary function is to restrict flow through the delivery lumen of the catheter).

As discussed herein, the systems and methods of the present invention rely on monitoring pressure during pulsed delivery of a fluid through a catheter. FIGS. 3-8 depict pressure measurements as a function of time in a variety of catheters to illustrate the principles of the present invention. It should be understood that these pressure curves are exemplary in nature only, for example, although scales may be included, the systems and methods of the present invention are not limited to catheters in which these same pressures are developed. Rather, it is the shape and/or amplitudes of the curves relative to a normal pressure curve taken in a properly functioning infusion system with an intact catheter that is free of unwanted obstructions, cuts, leaks, bubbles, etc. that can be used to identify catheter malfunctions in connection with the present invention.

Figure 3:
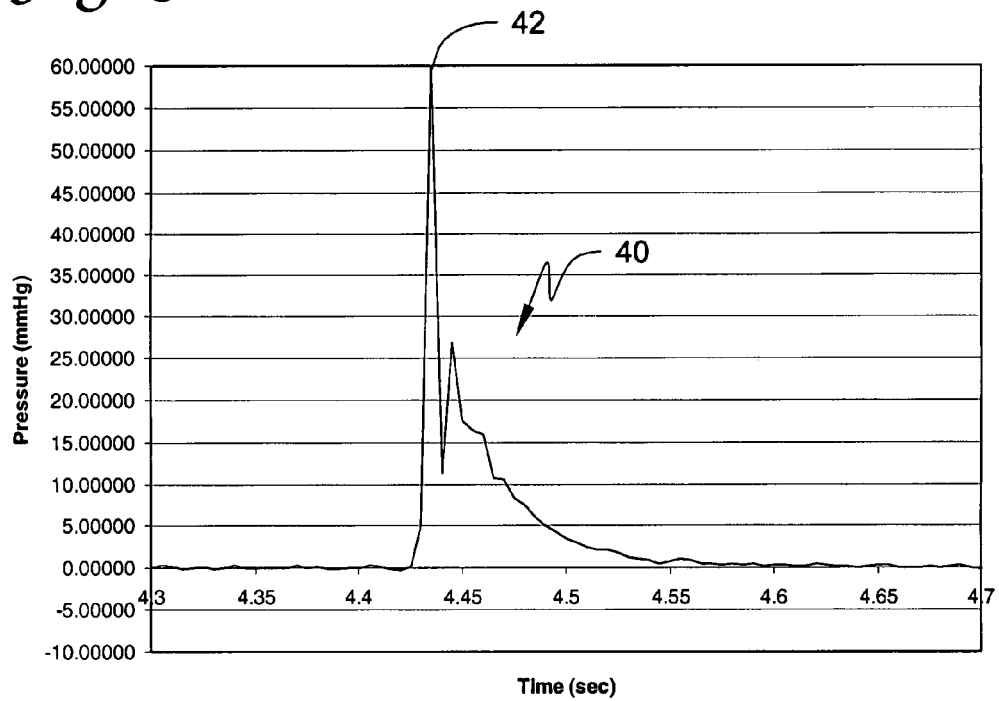
FIG. 3 is a graph of fluid pressure (y-axis) versus time (x-axis) in a properly functioning, intact catheter after a delivery pulse.

FIG. 3 depicts one exemplary normal pressure curve taken in one such properly functioning infusion system with an intact catheter that is free of unwanted obstructions, cuts, leaks, bubbles, etc. The pressure curve 40 includes a peak pressure 42 exhibited shortly after a pulsed bolus of fluid is delivered into the catheter by a pulsed delivery device. The pressure decays as the fluid is delivered by the catheter, eventually reaching a baseline pressure exhibited before the pulse. If a baseline pressure measurement is to be used, the baseline pressure measurement may preferably take place shortly before the pulse delivery event, e.g., between times 4.3 and 4.4 in FIG. 3.

Figure 4:
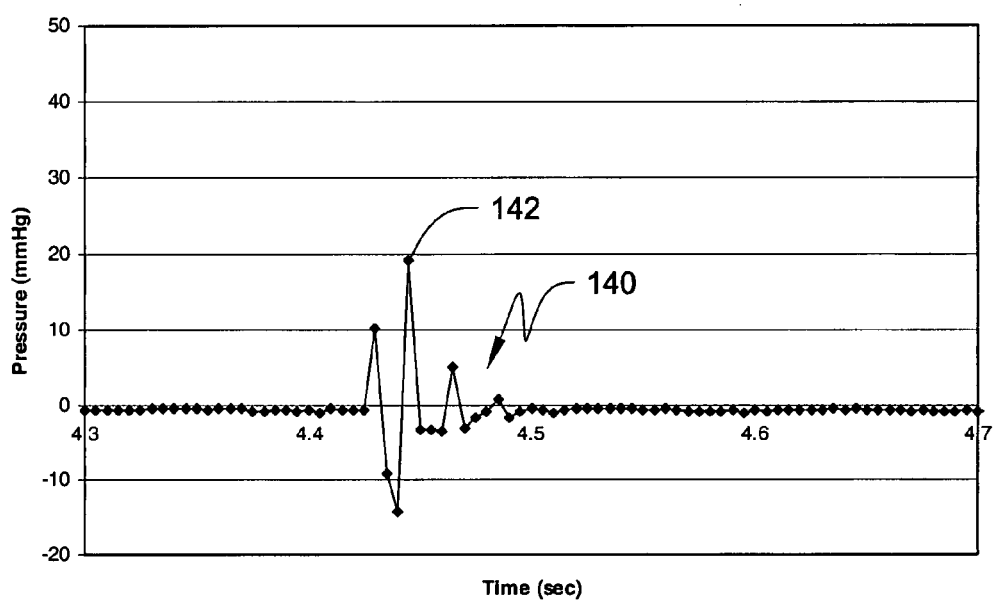
FIG. 4 is a graph of fluid pressure versus time detected after a delivery pulse when a catheter is disconnected from the infusion device.

The pressure curve 140 depicted in FIG. 4 provides an exemplary embodiment of a pressure curve exhibited by a system in which the catheter has become disconnected from the medical device used to deliver fluid. The pressure detected by the pressure sensor (located within, e.g., the medical device or at another location upstream from the point of disconnection) reaches a peak pressure 142 that is significantly lower than the peak pressure measured by in a properly functioning system (approximately one-third in the depicted pressure curves) and furthermore decays through the baseline pressure level much more rapidly than for an intact catheter.

In addition, the pressure curve 140 also exhibits a negative pressure peak (i.e., pressure below the baseline) in which the pressure falls below the baseline pressure after the delivery pulse. It may be preferred that the occurrence of a negative pressure peak be measured relative to a threshold pressure value that is below the baseline pressure eventually reached by both pressure curves 40 and 140.

Yet another difference between the disconnected pressure curve 140 and the normal pressure curve 40 (depicted in FIG. 3) is that the peak pressure 142 in the disconnected pressure curve 140 is actually a second peak reached after a first smaller peak.

In view of the differences between the pressure curve 40 and pressure curve 140, one method of determining the occurrence of a disconnected catheter may include, e.g., comparing the peak pressure developed after a delivery pulse with a selected peak pressure value. If the peak positive pressure developed at or after a delivery pulse is below a selected peak pressure value and the pressure falls below a selected negative pressure threshold after the delivery pulse, then a determination may be made that the catheter is disconnected.

A further characteristic that may be relied on to lead to a determination that a catheter is disconnected is that the catheter pressure successively rises above and falls below the baseline pressure during a pulse delivery event. In the illustrated example of FIG. 4, the pressure reading rises above and falls below the baseline pressure multiple times in rapid succession before eventually returning to the baseline pressure.

In such a method, the selected peak pressure value may be determined by any of a variety of techniques, e.g., the preceding peak pressure measurement, an average of all peak pressure measurements, a rolling average of a selected number of preceding peak measurements, etc. Alternatively, the selected peak pressure may not be a function of the specific system, i.e., the selected peak pressure value may be based on a predetermined value that does not require measurement of the infusion system in use.

Figure 5:
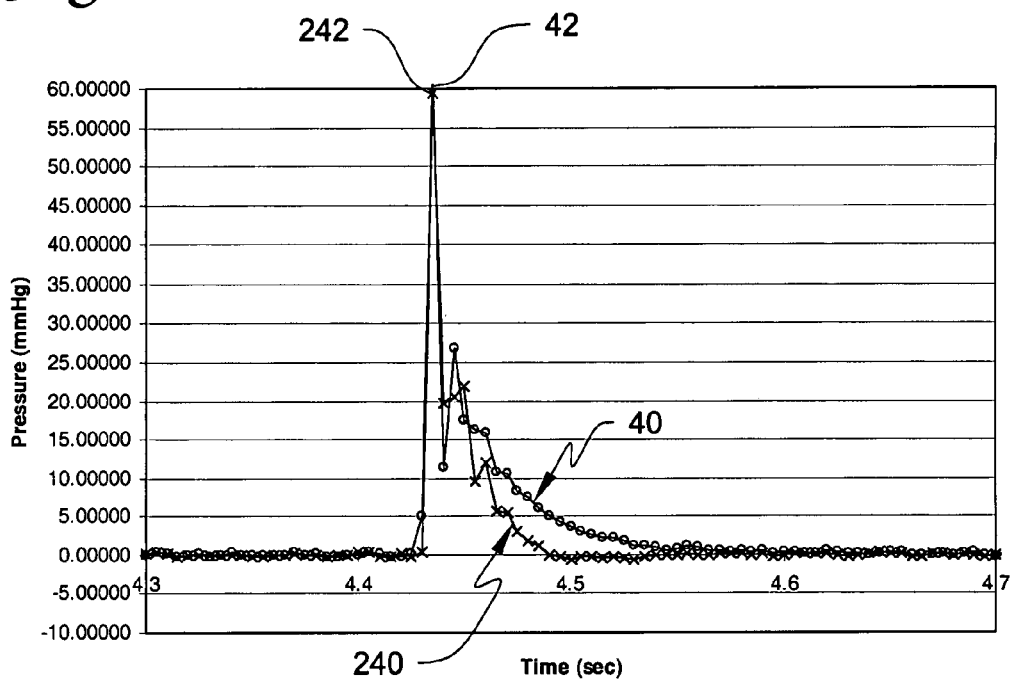
FIG. 5 is a graph of fluid pressure versus time after a delivery pulse in both a properly functioning, intact catheter and a catheter including a leak.

FIG. 5 depicts a pressure curve 242 developed in a catheter that includes a leak along with the pressure curve 40 developed in a properly functioning catheter. For purposes of the present invention, a leak may include a cut, tear, hole, etc. through which the fluid escapes from the delivery lumen of the catheter in place of or in addition to the delivery region 23. Although described in the singular, the catheter may include more than one leak. Furthermore, the leak may be present almost anywhere along the length of the delivery lumen, although a large cut or tear near the point at which the catheter connects to the medical device may result in a pressure curve more comparable to that developed by a disconnected catheter (see, e.g., FIG. 3). With reference to FIG. 2, the leak may be present between the delivery region 23 and the medical device 16 delivering fluid into the catheter 22, although the leak may also or alternatively be located downstream or past (distal of) the delivery region 23 of the catheter 22. In some instances, a leak may also be sensed if it occurs upstream of the pressure sensor.

In the presence of a leak, the pressure curve 240 may exhibit a peak pressure 242 that is similar to the peak pressure 42 of the normal pressure curve 40. The pressure curve 240 also decays as does the normal pressure curve 40. A difference is, however, that the rate of decay of the leak pressure curve 240 is faster than the corresponding normal pressure curve 40. This is also illustrated in connection with FIG. 6 which is an enlarged portion of the graph of FIG. 5.

The two pressure curves 40 and 240 may be described in terms of decay time during which the pressure in the delivery lumen of the catheter drops from the peak pressure to a threshold pressure 50. It may be preferred that the threshold pressure 50 be greater than the baseline pressure eventually reached by both pressure curves 40 and 240, although in some instances, the threshold pressure may be equal to the baseline pressure.

Figure 6:
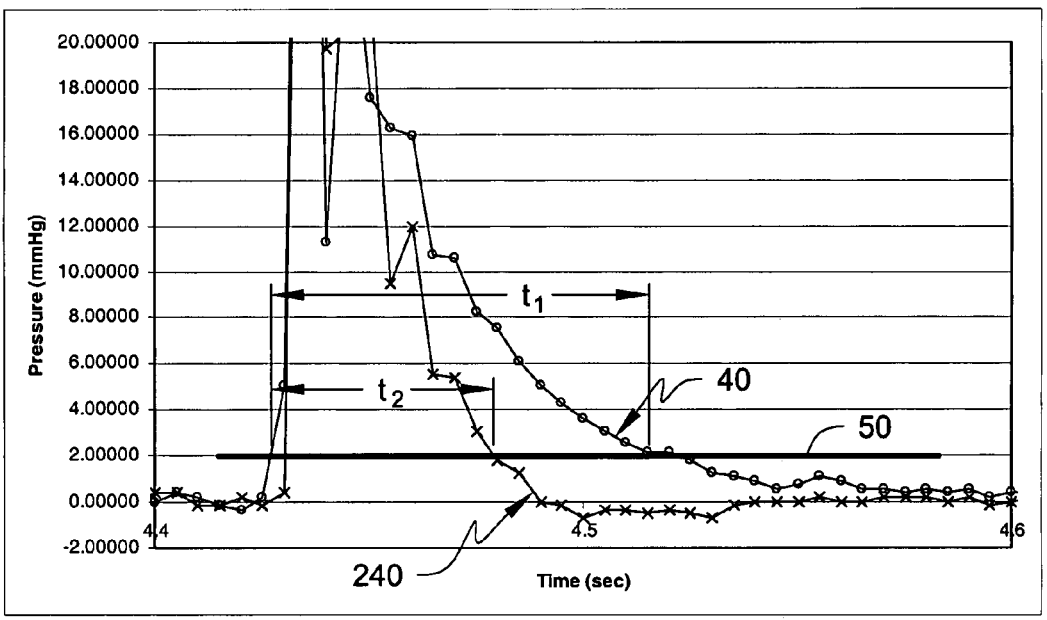
FIG. 6 is an enlarged view of a portion of the graph of FIG. 5, indicating decay time measurements $t_1$ and $t_2$ that can be used in connection with the present invention.

As depicted in FIG. 6, the decay time $t_1$ is the time required for the pressure in the normal curve 40 to reach the threshold pressure 50. The decay time of the leak pressure curve 240 is denoted by time $t_2$ on FIG. 6. The point from which the decay times may be determined based on a variety of different events. Examples of some potentially suitable events that may be used to initiate a measurement of decay time may be, e.g., the time at which a signal is sent to the pump mechanism to initiate a pulse delivery event, the time at which the pressure passes the threshold pressure (or another selected pressure) before reaching the peak pressure, etc.

In view of the differences between the pressure curve 40 and leak pressure curve 240, one method of identifying the occurrence of a leak in the catheter may include, e.g., comparing the decay time after a delivery pulse with a selected decay time. The selected decay time may be determined by any of a variety of techniques, e.g., the preceding decay time, an average of all decay times, a rolling average of a selected number of preceding decay times, etc. Alternatively, the selected decay time may not be a function of the specific system, i.e., the selected decay time may be based on a predetermined value that does not require measurement of the infusion system in use.

Figure 7:
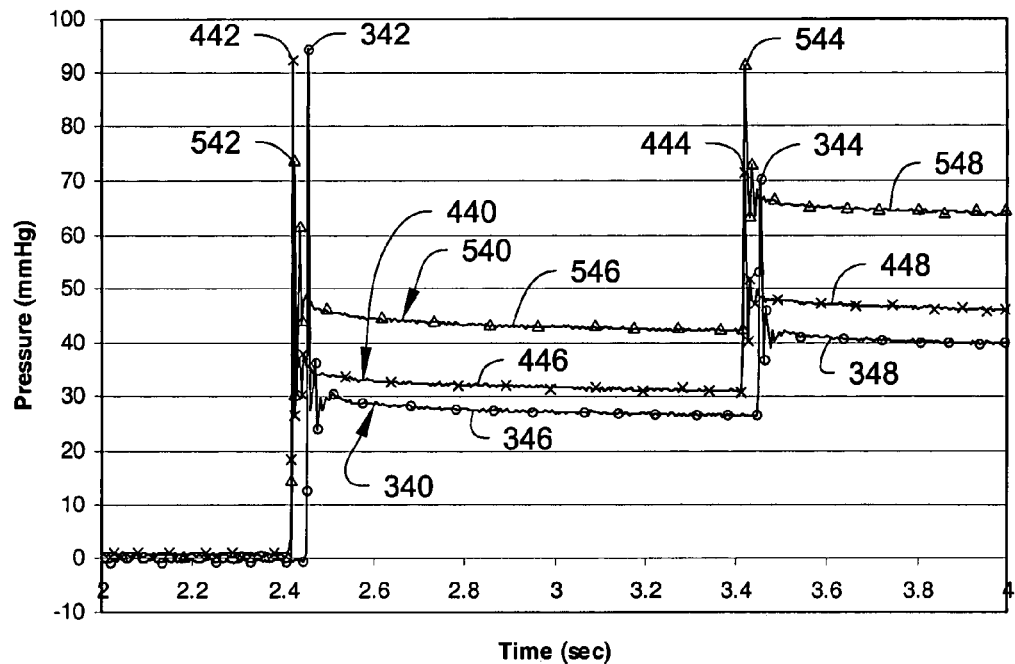
FIG. 7 is a graph of fluid pressure after two delivery pulses for catheters, each of which includes a blockage in different locations along the length of the delivery lumen.

Another catheter malfunction that be detected in connection with the present invention is the occurrence of a blockage in the delivery lumen downstream of the pump mechanism and the location at which the pressure measurement is taken. FIG. 7 depicts blocked pressure curves in which blockages are located in various locations along the length of the catheter.

The pressure curve 340, for example, is indicative of a blockage located proximate the distal end of the catheter. The pressure curve 340 reaches a peak 342 and then drops to an elevated pressure 346 that does not decay to the baseline present before the pulse delivery event. A second pulse delivery then raises the pressure in the catheter to a second peak 344 followed by a drop to a second elevated pressure 348 that is even higher than the first elevated pressure 346.

The pressure curve 440 is indicative of a blockage located approximately midway between the medical device 16 and the distal end of the catheter 22 (with reference to FIG. 2). The pressure curve 440 reaches a peak 442 and then drops to an elevated pressure 446 that does not decay to the baseline present before the pulse delivery event. A second pulse delivery then raises the pressure in the catheter to a second peak 444 followed by a drop to a second elevated pressure 448 that is even higher than the first elevated pressure 446.

The pressure curve 540 is indicative of a blockage located approximately midway between the medical device 16 and the distal end of the catheter 22 (with reference to FIG. 2). The pressure curve 540 reaches a peak 542 and then drops to an elevated pressure 546 that does not decay to the baseline present before the pulse delivery event. A second pulse delivery then raises the pressure in the catheter to a second peak 544 followed by a drop to a second elevated pressure 548 that is even higher than the first elevated pressure 546.

In the event a blockage occurs, all of the pressure curves depicted in FIG. 7 exhibit similarities in that the pressure does not decay to the baseline present before the first pulse delivery event after the blockage. It is theorized that the pressure does not decay to the baseline because the fluid is trapped within the catheter by the blockage. Because the pressure does not drop below a threshold pressure (see threshold 50 in FIG. 6), the decay time cannot be measured (it is essentially infinite). In an infusion system, the decay time may preferably be set at a selected timeout value if the pressure fails to drop below a selected threshold value after a selected time (typically at least two or more times value to in FIG. 6).

In view of the differences between a normal pressure curve as depicted in, e.g., FIG. 3 and the blocked pressure curves depicted in FIG. 7, one method of identifying the occurrence of a blockage in the catheter may include, e.g., determining if the decay time is at the timeout value set for the decay time measurement. If the decay time is at the timeout value, then the occurrence of a blockage in the catheter may be indicated.

In some infusion systems and methods of the present invention, it may be possible to determine where along the length of the catheter a blockage is located. As illustrated by the pressure curves 340, 440, and 540, the elevated pressures in the catheter after the delivery pulses can be correlated to the general location of the blockage, with the elevated pressure between peak pressures being generally higher as the blockage approaches the proximal end of the catheter (where the proximal end is the end attached to the medical device containing the pump mechanism).

Figure 8:
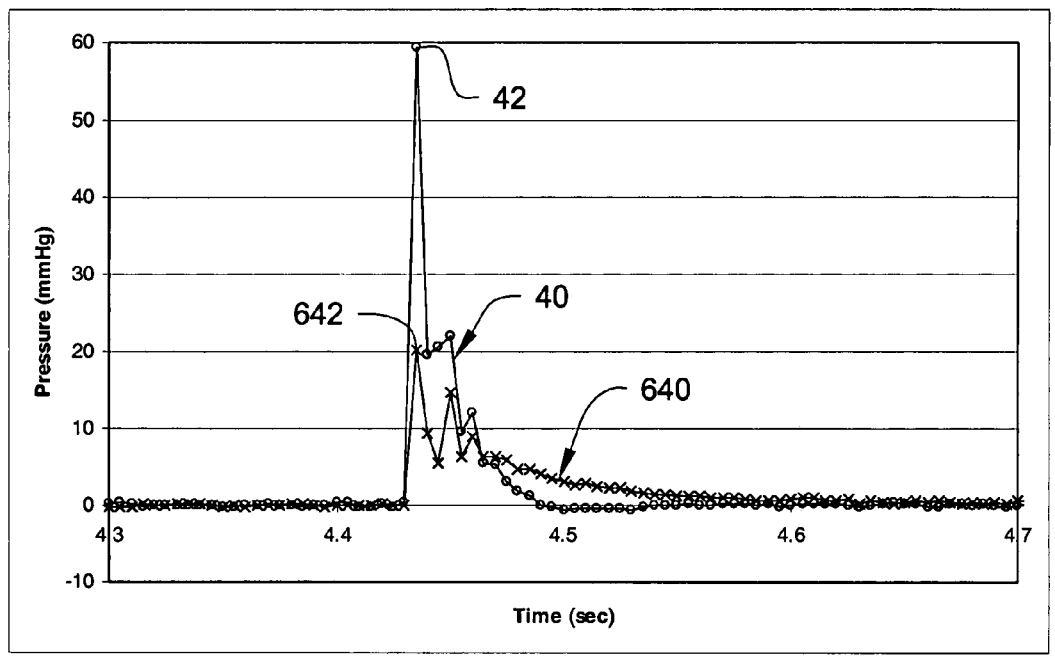
FIG. 8 is a graph of fluid pressure versus time detected after a delivery pulse in both a properly functioning, intact catheter and a catheter including a gas bubble in the delivery lumen.

FIG. 8 depicts a pressure curve 642 developed in a catheter that includes a gas bubble along with the pressure curve 40 developed in a properly functioning catheter that is being used to deliver a fluid in liquid form.

In the presence of a bubble, the pressure curve 640 may exhibit a peak pressure 642 that is significantly lower than the peak pressure 42 of the normal pressure curve 40. Although a reduced peak pressure is also seen in a catheter disconnection (see, e.g., FIG. 4), the pressure within the catheter containing the bubble remains above the baseline pressure (unlike pressure curve 140) and still decays to the baseline pressure (although the decay time may be extended in comparison to the normal pressure curve).

In view of the differences between a normal pressure curve 40 and the pressure curve 640 exhibited in the presence of a bubble, one method of identifying the occurrence of a bubble in the catheter may include, e.g., comparing the peak pressure developed after a delivery pulse with a selected peak pressure value. If the peak pressure developed at after a delivery pulse is below a selected peak pressure value and the pressure remains above a selected negative pressure threshold (unlike the pressure curve 140 of a disconnected catheter as seen in FIG. 4), then a determination may be made that a bubble is present in the catheter.

In methods relying on peak pressure values for malfunction determinations, the selected peak pressure value may be determined by any of a variety of techniques, e.g., the preceding peak pressure measurement, an average of all peak pressure measurements, a rolling average of a selected number of preceding peak measurements, etc. Alternatively, the selected peak pressure may not be a function of the specific system, i.e., the selected peak pressure value may be based on a predetermined value that does not require measurement of the infusion system in use.

In some systems and methods, it may be preferred, in the presence of a reduced peak pressure, to make a determination that either the catheter is disconnected or a bubble is present and provide an appropriate signal or take some other action. Distinguishing between the presence of a bubble or a disconnected catheter may then be made by other techniques such as, e.g., inspection by a medical practitioner, etc.

Figure 9:
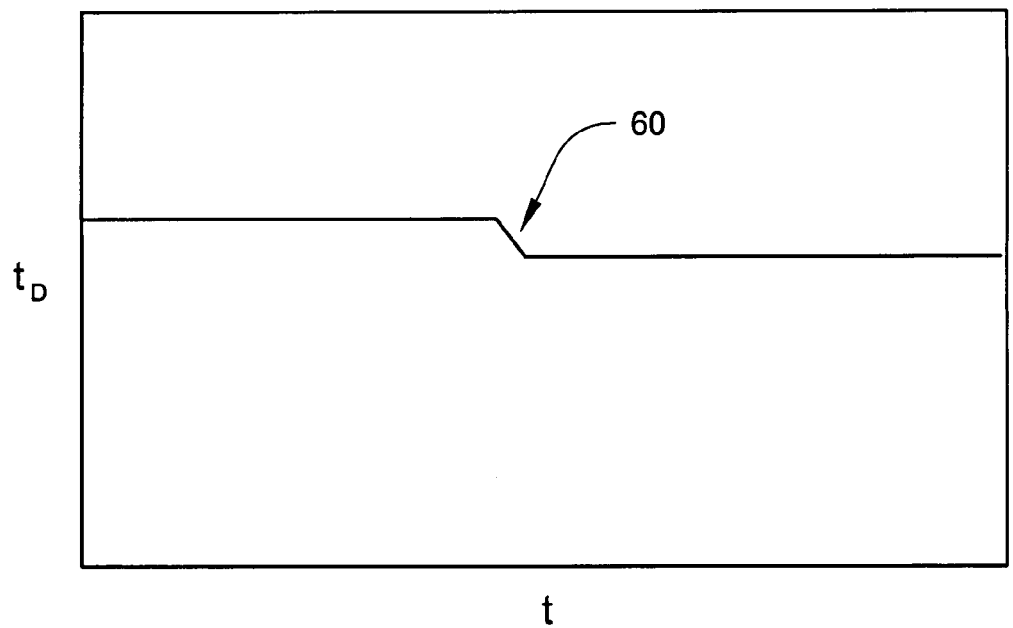
FIG. 9 is a graph of decay times as a result of pulsed delivery of fluid into a catheter including a leak.

FIG. 9 depicts a graph of decay times ($t_D$) measured over time (t) to illustrate a method determining the presence of a leak in a catheter. As can be seen in FIG. 9, the decay times will typically remain relatively constant up to the occurrence of a leak in the catheter. At region 60, however, a leak develops which results in a deflection in the graph with the decay times dropping (see the discussion regarding FIGS. 5 & 6 above). Data such as that depicted in FIG. 9 may be stored in the medical device (or elsewhere) for later retrieval and/or review to determine the existence of a catheter malfunction in the form of a leak.

Figure 10:
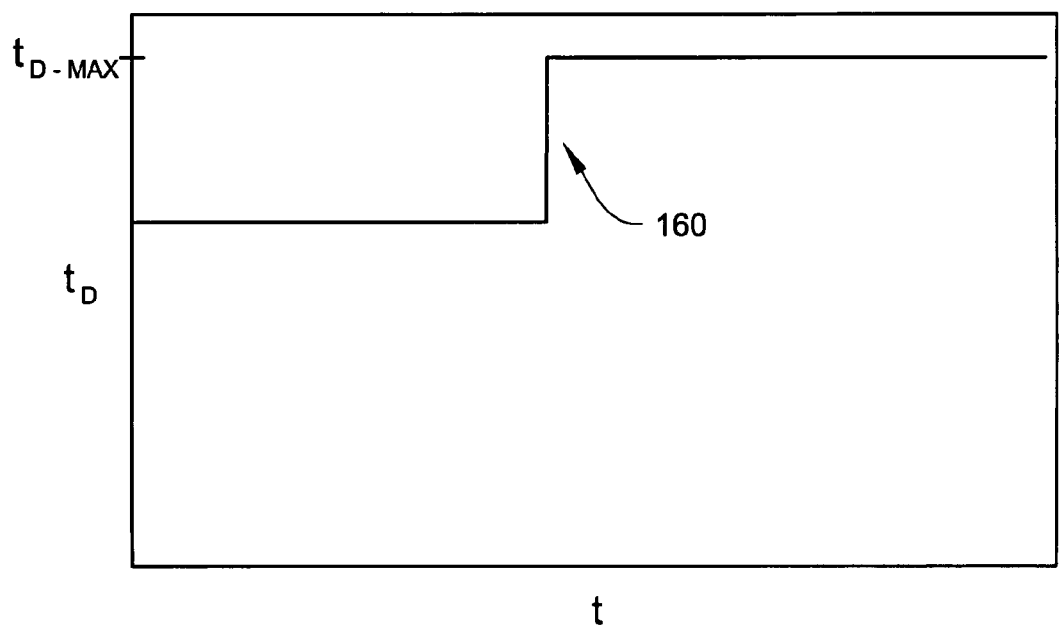
FIG. 10 is a graph of decay times as a result of pulsed delivery of fluid into a blocked catheter.

FIG. 10 also depicts a graph of decay times ($t_D$) measured over time (t) to illustrate a method determining the presence of a blockage in a catheter. As can be seen in FIG. 10, the decay times will typically remain relatively constant up to the occurrence of a blockage in the catheter. At region 160, however, a blockage develops which results in a deflection in the graph with the decay times rising to the timeout value ($t_{D-max}$) (see the discussion regarding FIG. 7 above). Data such as that depicted in FIG. 10 may be stored in the medical device (or elsewhere) for later retrieval and/or review to determine the existence of a catheter malfunction in the form of a blockage.

Figure 11:
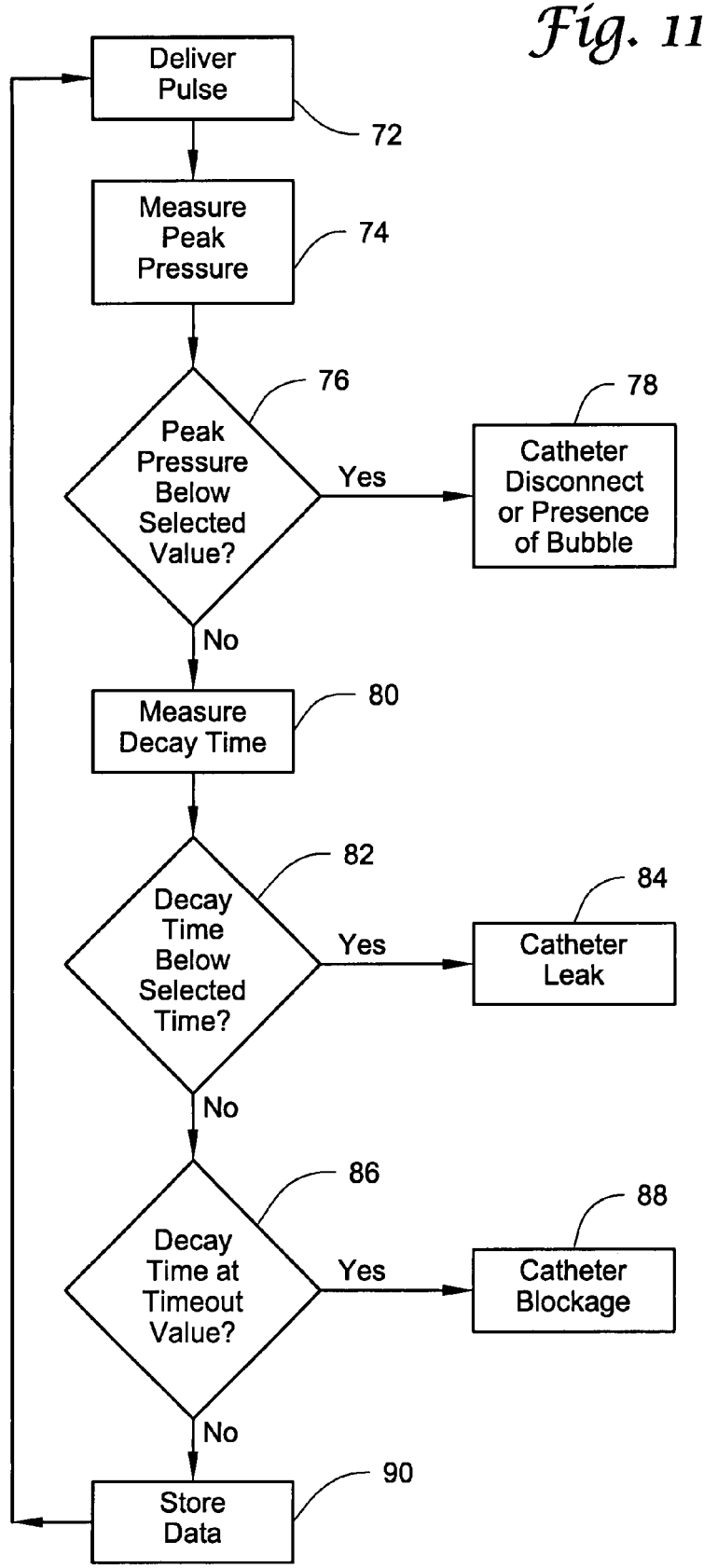
FIG. 11 is a flowchart of one method of determining a variety of catheter malfunctions in accordance with the present invention.

FIG. 11 is a flowchart depicting one method of determining the existence and type of malfunction in a catheter, with the method capable of distinguishing between a variety of different malfunctions. At 72, the method includes delivering a pulse or bolus of fluid into a catheter. The pulse delivery 72 is followed by a measurement of the peak pressure developed after the pulse 74. The measured peak pressure may then be compared to a selected value for the peak pressure 76 as discussed herein. If the measured peak pressure is below the selected value, then a determination can be made that the catheter is either disconnected or that a gas bubble is present 78.

If the measured peak pressure is above the selected value, then the decay time can be measured 80 as discussed herein. If the decay time (the time required for the pressure to fall below a selected threshold value) is below a selected time 82, than a determination can be made that a leak is present in the catheter 84.

If the decay time as measured above 80 is at a selected timeout value 86, then a determination can be made that the catheter contains a blockage in the fluid delivery pathway 88.

The data (e.g., peak pressure and/or decay time) may then be stored for use in, e.g., generating graphs such as those depicted in FIGS. 9 & 10 or for any other purpose. Other purposes may include calculating averages, rolling averages, etc.

In the event that it is determined that a malfunction exists, a variety of actions may be taken. For example, the delivery of the fluid may be terminated, the rate of delivery of the fluid may be changed, etc. In addition to or in place of terminating or changing the fluid delivery, other actions may be taken. For example, an alert may be provided to the patient and/or a third party (caregiver, medical personnel, etc.). The alert may be provided locally in the form of an audible signal, etc., or it may be transmitted from the infusion system to another device, e.g., personal computer, modem, etc.

The complete disclosure of the patents, patent documents, and publications cited in the Background, the Detailed Description of Exemplary Embodiments, and elsewhere herein are incorporated by reference in their entirety as if each were individually incorporated.

Illustrative embodiments of this invention are discussed and reference has been made to possible variations within the scope of this invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

The invention claimed is:

1. A method of identifying the presence of a catheter malfunction, the method comprising:
    delivering pulses of a fluid into a delivery lumen of an implanted catheter;
    measuring decay time after a selected pulse, wherein the decay time is the time required for pressure within the delivery lumen to fall below a selected threshold pressure value after a selected event corresponding to the selected pulse;
    comparing the decay time to a selected decay time; and
    determining the existence of a catheter malfunction in the form of a leak in the catheter if the decay time is below the selected decay time.

2. A method according to claim 1, further comprising:
    assigning a timeout value to the decay time if the pressure within the delivery lumen does not fall below the selected threshold pressure value after a selected timeout time; and
    determining the existence of a catheter malfunction in the form of a blockage in the delivery lumen if the decay time is assigned the timeout value.

3. A method according to claim 1, further comprising providing an alert to the patient and/or a third party after determining the existence of the catheter malfunction.

4. A method according to claim 1, further comprising terminating delivery of the fluid after determining the existence of the catheter malfunction.

5. A method according to claim 1, wherein the selected decay time comprises an average of a plurality of measured decay times obtained before the selected event.

6. A method according to claim 1, wherein the selected event comprises the time at which a signal is sent to a pump mechanism to deliver the selected pulse into the catheter.

7. A method according to claim 1, wherein the selected event comprises the time at which pressure in the delivery lumen reaches the selected threshold pressure before reaching a peak pressure after the selected pulse.

8. A method according to claim 1, further comprising determining a baseline pressure before the selected pulse and after a pulse that precedes the selected pulse.

9. A method of identifying the presence of a catheter malfunction, the method comprising:
    delivering pulses of a fluid into a delivery lumen of an implanted catheter;
    measuring decay time after a selected pulse, wherein the decay time is the time required for pressure within the delivery lumen to fall below a selected threshold pressure value after a selected event corresponding to the selected pulse; and
    assigning a timeout value to the decay time if the pressure within the delivery lumen does not fall below the selected threshold pressure value after a selected timeout time.

10. A method according to claim 9, further comprising determining the existence of a catheter malfunction in the form of a blockage in the delivery lumen if the decay time is assigned the timeout value.

11. A method according to claim 10, further comprising providing an alert to the patient and/or a third party after determining the existence of the catheter malfunction.

12. A method according to claim 10, further comprising terminating delivery of the fluid after determining the existence of the catheter malfunction.

13. A method according to claim 9, wherein the selected event comprises the time at which a signal is sent to a pump mechanism to deliver the selected pulse into the catheter.

14. A method according to claim 9, wherein the selected event comprises the time at which pressure in the delivery lumen reaches the selected threshold pressure before reaching a peak pressure after the selected pulse.

15. A method according to claim 9, further comprising determining a baseline pressure before the selected pulse and after a pulse that precedes the selected pulse.

16. A method of identifying the presence of a catheter malfunction, the method comprising:
    delivering pulses of a fluid into a delivery lumen of an implanted catheter;
    measuring peak pressure within the delivery lumen after a selected pulse;
    comparing the measured peak pressure to a selected peak pressure value; and
    determining the existence of a catheter malfunction in the form of a disconnected catheter if the measured peak pressure value is below the selected peak pressure value.

17. A method according to claim 16, further comprising providing an alert to the patient and/or a third party after determining the existence of the catheter malfunction.

18. A method according to claim 16, further comprising terminating delivery of the therapeutic substance after determining the existence of the catheter malfunction.

19. A method according to claim 16, wherein the selected peak pressure value comprises an average of a plurality of measured peak pressures obtained before the selected pulse.

20. A method according to claim 16, wherein the selected peak pressure value comprises a rolling average of a plurality of measured peak pressure values obtained before the selected pulse.

21. A method according to claim 16, further comprising determining a baseline pressure before the selected pulse and after a pulse that precedes the selected pulse.

22. A method of determining the presence of a catheter malfunction, the method comprising:
    delivering pulses of the fluid into a delivery lumen of the catheter; measuring peak pressure within the delivery lumen after a selected pulse;
    comparing the measured peak pressure to a selected peak pressure value;
    determining the existence of a catheter malfunction in the form of a disconnected catheter if the measured peak pressure value is below the selected peak pressure value after comparing the measured peak pressure to the selected peak pressure;
    measuring decay time after a selected pulse, wherein the decay time is the time required for pressure within the delivery lumen to fall below a selected threshold pressure value after a selected event corresponding to the selected pulse;
    assigning a timeout value to the decay time if the pressure within the delivery lumen does not fall below the selected threshold pressure value after a selected timeout time;
    comparing the decay time to a selected decay time after measuring the decay time;

determining the existence of a catheter malfunction in the form of a leak in the catheter if the decay time is below the selected decay time; and determining the existence of a catheter malfunction in the form of a blockage in the delivery lumen if the decay time is at the timeout value.

23. An implantable infusion system comprising:
a pump mechanism fluidly coupled to a reservoir to receive fluid contained within the reservoir;
a catheter comprising a delivery lumen fluidly coupled to the pump mechanism, wherein the delivery lumen extends to a delivery region in the catheter;
a pressure sensor positioned to monitor fluid pressure within the delivery lumen of the catheter and provide a pressure signal representative of the fluid pressure; and
control electronics operably coupled to the pump mechanism and connected to receive the pressure signal from the pressure sensor, wherein the system, via the control electronics, pump mechanism and pressure sensor, is configured to carry out the method of claim 1.

24. A system according to claim 23, wherein the pump mechanism, the reservoir, and the control electronics are contained within one or more implantable housings along with a power source.

25. An implantable infusion system comprising:
a pump mechanism fluidly coupled to a reservoir to receive fluid contained within the reservoir;
a catheter comprising a delivery lumen fluidly coupled to the pump mechanism, wherein
the delivery lumen extends to a delivery region in the catheter;
a pressure sensor positioned to monitor fluid pressure within the delivery lumen of the catheter and provide a pressure signal representative of the fluid pressure; and
control electronics operably coupled to the pump mechanism and connected to receive the pressure signal from the pressure sensor, wherein the system, via the control electronics, pump mechanism and pressure sensor, is configured to carry out the method of claim 9.

26. A system according to claim 25, wherein the pump mechanism, the reservoir, and the control electronics are contained within one or more implantable housings along with a power source.

27. An implantable infusion system comprising:
a pump mechanism fluidly coupled to a reservoir to receive fluid contained within the reservoir;
a catheter comprising a delivery lumen fluidly coupled to the pump mechanism, wherein the delivery lumen extends to a delivery region in the catheter;
a pressure sensor positioned to monitor fluid pressure within the delivery lumen of the catheter and provide a pressure signal representative of the fluid pressure; and
control electronics operably coupled to the pump mechanism and connected to receive the pressure signal from the pressure sensor, wherein the system, via the control electronics, pump mechanism and pressure sensor, is configured to carry out the method of claim 16.

28. A system according to claim 27, wherein the pump mechanism, the reservoir, and the control electronics are contained within one or more implantable housings along with a power source.

* * * * *